United States Patent [19]

Rincoe et al.

[11] Patent Number: 5,253,656
[45] Date of Patent: Oct. 19, 1993

[54] APPARATUS AND METHOD FOR MONITORING CONTACT PRESSURE BETWEEN BODY PARTS AND CONTACT SURFACES

[76] Inventors: Richard G. Rincoe, 49 South Homlman Way, Golden, Colo. 80401; Paul J. Moore, Jr., 890 Moline St., Aurora, both of Colo. 80010

[21] Appl. No.: 704,615

[22] Filed: May 23, 1991

[51] Int. Cl.⁵ .............................................. A61B 5/103
[52] U.S. Cl. ..................................... 128/782; 73/172
[58] Field of Search ............... 128/774, 779, 782, 748; 73/172, 862.04; 623/33, 35, 36, 66, 901; 364/556, 558, 413.01, 413.02

[56] References Cited

U.S. PATENT DOCUMENTS

| | | | |
|---|---|---|---|
| 3,732,578 | 5/1973 | Pollack | 128/774 |
| 3,974,491 | 8/1976 | Sipe | 340/272 |
| 4,057,056 | 11/1977 | Payton | 128/83.5 |
| 4,195,643 | 4/1980 | Pratt, Jr. | 128/779 |
| 4,250,894 | 2/1981 | Frei et al. | 128/774 |
| 4,267,728 | 5/1981 | Manley et al. | 73/172 |
| 4,421,124 | 12/1983 | Marshall | 128/782 |
| 4,426,884 | 1/1984 | Polchaninoff | 73/172 |
| 4,509,527 | 4/1985 | Fraden | 128/671 |
| 4,554,930 | 11/1985 | Kress | 128/774 |
| 4,633,237 | 12/1986 | Tucknott et al. | 340/573 |
| 4,696,780 | 9/1987 | Hägglund | 264/222 |
| 4,794,935 | 1/1989 | Viesturs | 128/774 |
| 4,814,661 | 3/1989 | Ratzlaff et al. | 310/328 |
| 4,819,660 | 4/1989 | Smith | 128/774 |
| 4,869,265 | 9/1989 | McEwen | 128/774 |
| 4,988,360 | 1/1991 | Shamp | 623/33 |
| 5,010,772 | 4/1991 | Bourland et al. | 73/862.04 |
| 5,010,774 | 4/1991 | Kikuo et al. | 73/862.04 |
| 5,060,174 | 10/1991 | Gross | 364/558 |
| 5,127,420 | 7/1992 | Horvath | 128/782 |
| 5,170,364 | 12/1992 | Gross et al. | 364/558 |

FOREIGN PATENT DOCUMENTS 136247  4/1985  European Pat. Off. ............ 128/774

Primary Examiner—Max Hindenburg
Assistant Examiner—Guy V. Tucker
Attorney, Agent, or Firm—Timothy J. Martin; Dana S. Rewoldt

[57] ABSTRACT

An apparatus and method for monitoring pressure between the surface of a body part and a contact surface employ a plurality of pressure sensors disposed in a matrix array between the contact surface and the body part. The sensors produce analog force signals proportional to pressure, and a monitor receives the analog signals and produces output signals, preferably digital, having pressure data corresponding to the pressure at each sensor. A computer processor receives the output signals from the monitor to create a force profile for the sensor array. The sensors may be scanned as a read event in variety of manners, including periodic, continuous and triggered scanning. Where triggered scanning is desired, one or more switches act to initiate a read event. This monitoring apparatus and method is used, for example, to fit prosthetics, to monitor bed-ridden and wheelchair-bound patients, to reduce pain and sores caused by uneven distribution of pressure and to monitor pressure between a cast and a person. The sensors may be mounted on a single sheet or on strips for positioning along the body, and monitoring is accomplished by multiplexing and digitizing the analog force signals.

16 Claims, 5 Drawing Sheets

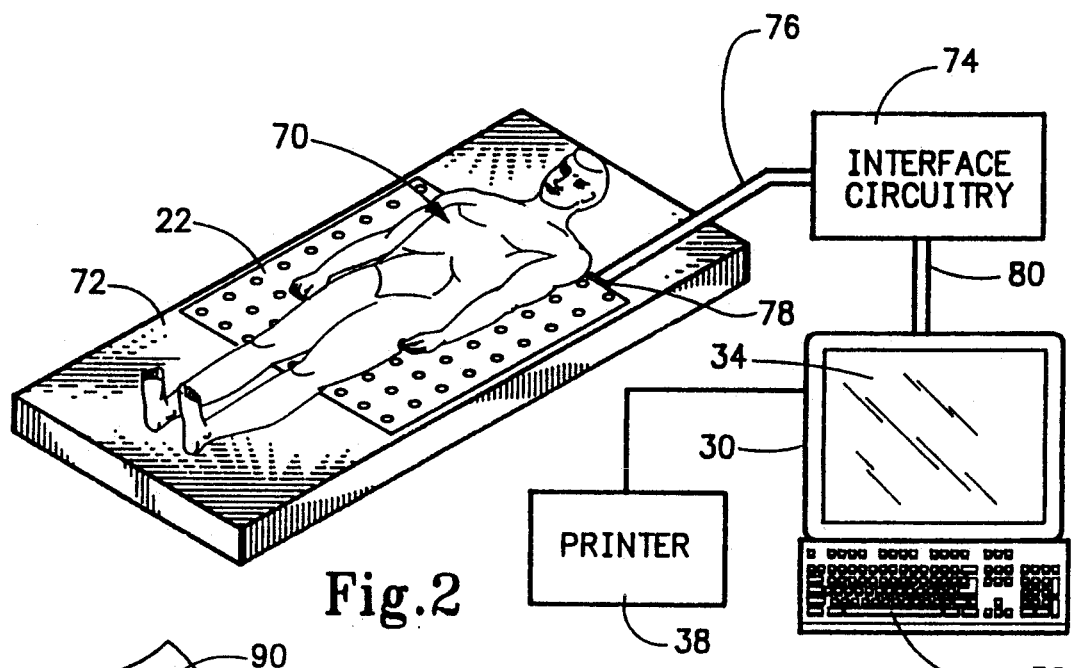
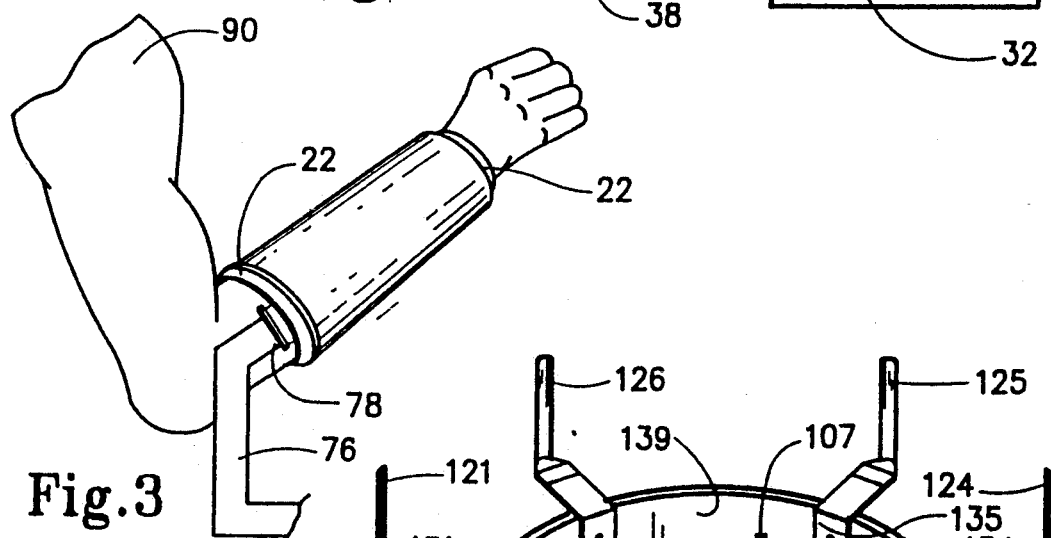
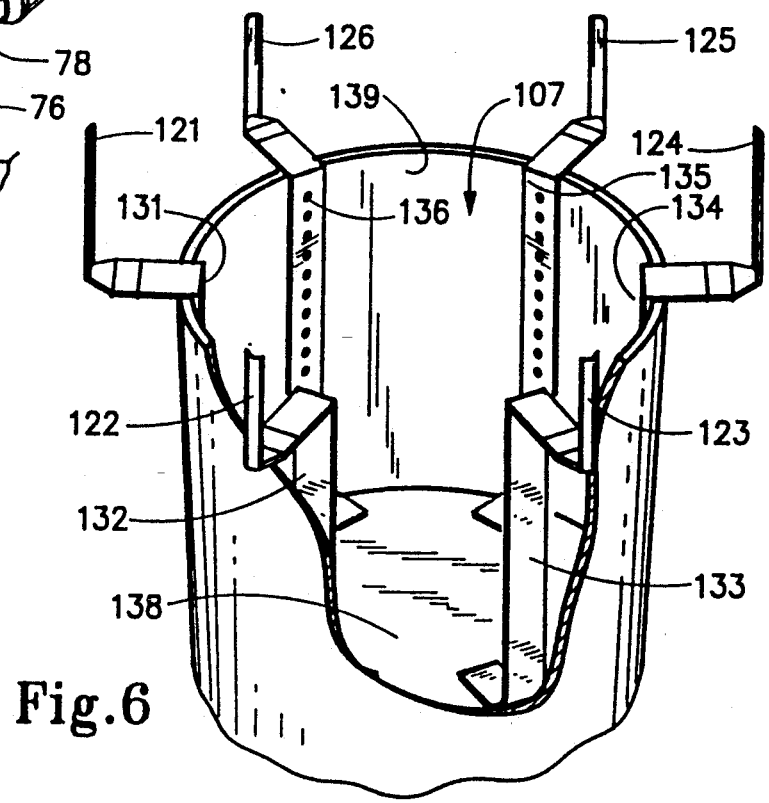

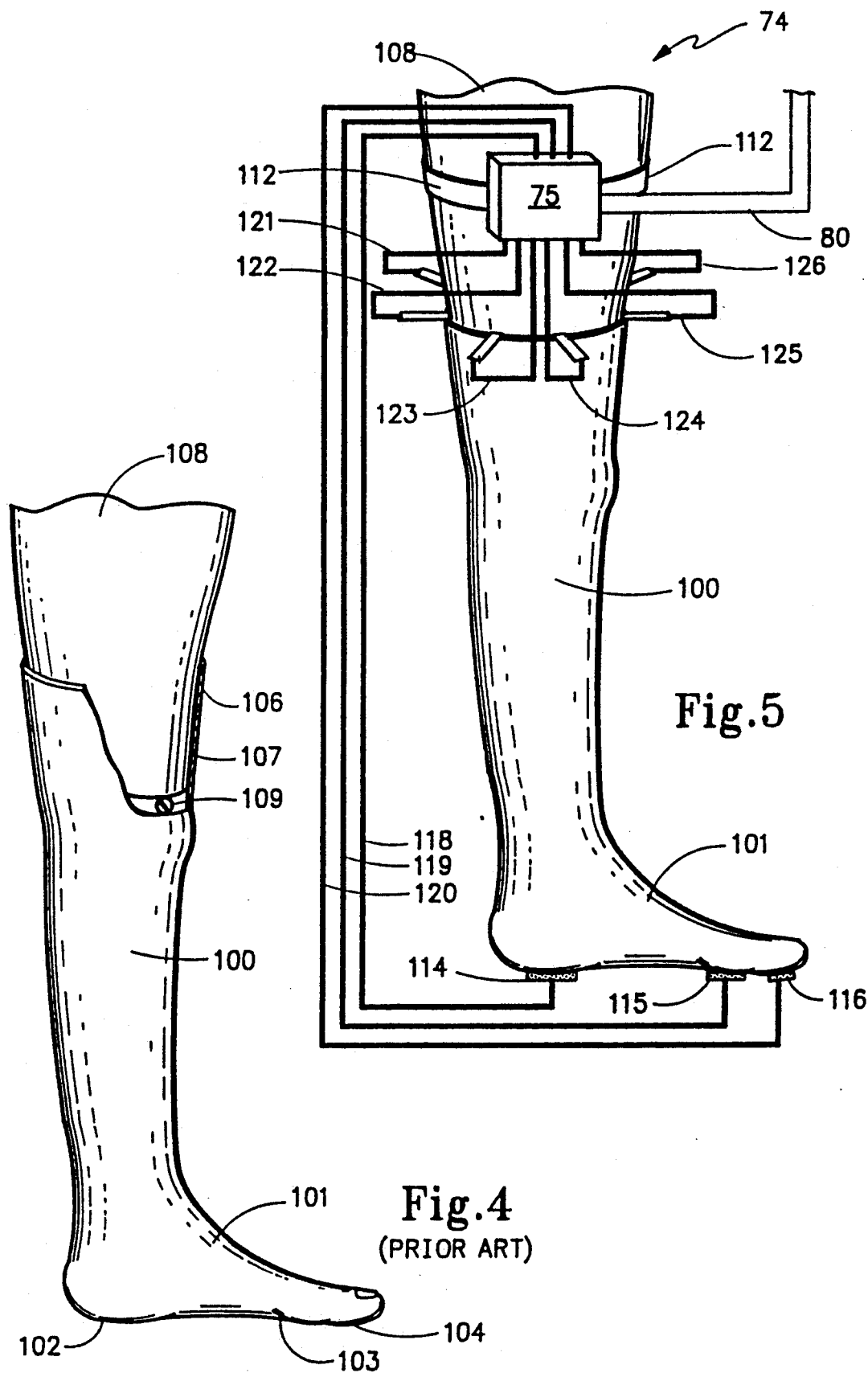

APPARATUS AND METHOD FOR MONITORING CONTACT PRESSURE BETWEEN BODY PARTS AND CONTACT SURFACES

FIELD OF INVENTION

The present invention generally relates to the monitoring of contact force between the exterior surface of a body part and another surface. Specifically, the present invention concerns the generation of a profile for the pressure applied to the outer surface of a body part, such as a weight bearing surface, in order to detect a non-uniform distribution of pressure which can result in excessive irritation or pain to the body part.

BACKGROUND OF THE INVENTION

It is well known that the goals of medicine include both the prevention and the treatment of illness and injury. Since some form of pain to the body often accompanies illnesses and injuries, treatment may include protocols that help suppress or eliminate such pain. Thus, the focus of treatment is mostly directed to this primary pain associated with the trauma of the illness or injury, itself.

However, it is not unusual during the course of treatment for the patient to be subjected to conditions that are not ordinary in day-to-day life. For example, severe injury or prolonged illness can often result in the confinement of the patient to a bed or to a wheel chair. Some injuries, such as broken bones, and even some illnesses, are treated by the application of a support cast to a portion of the body to immobilize and support the body portions during convalescence. In the case of loss of limbs or amputation, treatment may include the provision of an appliance, such as a prosthesis, which may be attached to the body. In each of these cases, a contact surface of the object bears against an exterior surface portion of a body part either due to the weight of the body against the support surface or due to the weight of the item against the body part. The force of gravity therefore creates a pressure which is distributed over the area or contact with this pressure having a magnitude dependent upon such parameters as the area and contour of the contacting surfaces, the weight of the object or the person, the orientation of the contact surfaces to the direction of gravitational force, friction between the surfaces, etc.

Typically, these contact forces are not uniformly distributed over the contacting surface areas so that some localized areas experience a greater pressure than other areas. Areas of greater pressure over small surface areas tend to traumatize the body part, and this trauma can produce aggravating pain to the individual. Indeed, this trauma can be to such an extent as to ulcerate the skin to produce sores which are not only painful but also which may become infected. Further, swelling of the body part approximate to the area of trauma can even increase pressure which only serves to exacerbate the pain and the risk of sores.

For example, when a person is confined to an article of furniture, such as a bed or wheel chair, bed sores may develop on the legs and torso due to the weight of the person against the support surface of the article of furniture. Different pressures may result in a cast due to swelling or shrinkage of a body part confined therein so that portions of the exterior surface of the body part may be subjected to greater pressures and abrasion than other portions; this can again result in pain or ulceration. A prosthesis is usually mounted by receiving the stump of a limb in a socket of the prosthesis so that pressure exists between a surface of the stump and the socket of the prosthesis. Changes in the body weight and musculature of the person resulting from use of the prosthesis may effect the fit of the prosthesis on the stump which again cause hot spots leading to pain and ulceration of the exterior surface of the stump.

Heretofore, it has not been known to monitor the force profile of pressure over the exterior surface of the body part which contacts a surface of another object, and apparatus to monitor this pressure distribution to provide a force profile is not known to the inventors. There has been a long felt need, though, for an apparatus method which can measure the pressure distribution to produce a force profile of the contacting surfaces either so, that a better fit of a cast or a prosthesis may be had or so that potential hot spots can be identified at an early stage thereby allowing medical personnel to alter the contour or the orientation of the contact surfaces in an effort to help reduce or eliminate the excessive pressure in the localized area. The present invention is directed to the provision of such apparatus and method.

SUMMARY OF THE INVENTION

It is an object of the present invention to provide a new and useful apparatus and method for the monitoring of pressure between a contact surface and the exterior surface of a body part which forcibly bears against the contact surface and to generate a force profile corresponding to the distribution of pressure between the two contacting surfaces.

Another object of the present invention is to provide apparatus which can be used to monitor the force distribution between a contact surface and an exterior surface of a body part so as to detect localized areas on the exterior surface of a body part which are being subjected to excessive forces.

A further object of the present invention is to provide apparatus and methodology which may be triggered to produce one or more "snap shots" of the force profile of force distribution between a contact surface and the exterior surface of a body part at a selected moment or upon the occurrence of a triggering event.

Still a further object of the present invention is to provide a method for achieving a better fit between a prosthesis, and particularly an artificial limb such as an artificial leg, onto the stump of an amputee.

To accomplish these objects, an apparatus and method is provided to monitor pressure at a plurality of locations along the exterior surface of a body part to produce a force profile corresponding to the distribution of force caused by pressure of the body part against the contact surface. In its broad form, the apparatus according to the present invention includes a plurality of pressure sensors which are organized in an array such that the sensors may be interposed between the exterior surface of the body part and the contact surface of selected locations at which pressure is to be monitored. Each of these pressure sensors is selected to respond to pressure between the surfaces to produce a force signal proportional to the pressure between the surfaces at the location of the sensor. A monitor communicates with the array of sensors and receives the force signal produced by each respective sensor. This monitor then generates an output signal indicative of the pressure sensed by a respective sensor according to its location.

A controller communicates with the monitor in order to receive and process the output signals in order to produce a force profile corresponding to the magnitude and location of the pressure exerted by the contact surface on the body part.

Preferably, the controller is a computer which can produce a read signal operative to instruct the monitor to provide the output signals to the computer as a read event. Correspondingly, the monitor includes circuitry, such as multiplexing circuitry, so that it can individually address each of the sensors in the array and so that it can individually access each sensor to receive a specific force signal corresponding to the location to that sensor. Preferably, the array of sensors is organized in a row and column format, and the monitor operates to consecutively communicate the output signals to the controller, for example for each sensor in a row.

One or more switches may be provided so that a read event occurs when both switch active signal is present and the controller has signaled for a read event. The data for each read event is then correlated to the specific switch that was active during the read event. To this end, the controller includes a memory for storing pressure data from each of the sensors doing each read event with the pressure data being correlated to the location of the respective sensor. Since the output signals of the monitor are normally digital signals, an analog to digital converter is provided to convert the analog force signals to digital force signals.

The pressure sensors are preferably mounted on at least one strip of flexible substrate material that is adapted to be disposed between the contact surface and the exterior surface of the body part so as to conform to the shape of the body part. A plurality of such strips may be spaced apart from one another along the surface to define the array, and each strip may accordingly define a column in the array of sensors. Alternately, the sensors may be mounted on a single sheet of material as a two dimensional array.

According to the methodology of the present invention a force profile is produced by the steps of interposing a plurality of pressure sensors at selected locations between the exterior surface of a body part and a contact surface at selected locations and then monitoring the pressure sensed by each of the pressure sensors in response to pressure forces between the exterior of the body part and the contact surface in order to generate an output signal corresponding to the force of pressure sensed by each sensor. These output signals are then received and stored as a read event after which the pressure data correlated to the location of each sensor may be displayed as a force profile which corresponds to the magnitude and location of the pressure exerted by the contact surface on the body part.

As with the above described apparatus, the broad methodology includes the positioning of the sensors in an array of rows and columns, and the step of monitoring the array may occur by scanning the sensors in each row, with each row then being consecutively scanned. The preferred methodology includes providing switches to initiate a read event. Where the methodology is used to fit an artificial leg to a stump, switches are provided at the heel, ball and toe portions of the prosthesis while the array of sensors is disposed within the socket of the prosthesis. Accordingly, the method includes the step of initiating a read event upon the consecutive actuation of the switches as the heel, ball and toe portion of the prosthesis strikes a walking surface while the person employs the prosthesis thereby generating an individual force profile corresponding to the heel strike, the ball strike and the toe strike.

These and other objects of the present invention will become more readily appreciated and understood from a consideration of the following detailed description of the preferred embodiment when taken together with the accompanying drawings, in which:

BRIEF DESCRIPTION OF THE DRAWINGS

FIG. 2 is a perspective view of a patient on a bed with use of the present invention being diagrammatically shown therewith;

FIG. 3 shows use of the present invention in monitoring pressure between a persons lower arm and an orthopedic cast;

FIG. 4 is a side view partially broken away, of an artificial leg as is known in the prior art;

FIG. 5 is a side view of the leg shown in FIG. 4 having attached thereto, in diagrammatic form, the preferred embodiment of the present invention used to monitor pressure between the leg stump and the artificial leg;

FIG. 6 is a perspective view, partially broken away, of the monitoring apparatus shown in FIG. 5;

DETAILED DESCRIPTION OF THE EXEMPLARY EMBODIMENTS

The present invention is directed to pressure monitoring apparatus and systems specifically adapted for monitoring the force of pressure of a body part against a contact surface such as an article of furniture (bed, chairs, wheel chairs, etc.), orthopedic casts and prostheses (such as artificial limbs). Pressure is monitored at a plurality of locations to create a force profile corresponding to the distribution of pressure, usually from weight caused by gravity, between the body part and the contact surface. This force may be the weight of the body on the contact surface, which serves as a support for the body, or it can be the weight of an item on the body part.

Figure 1:
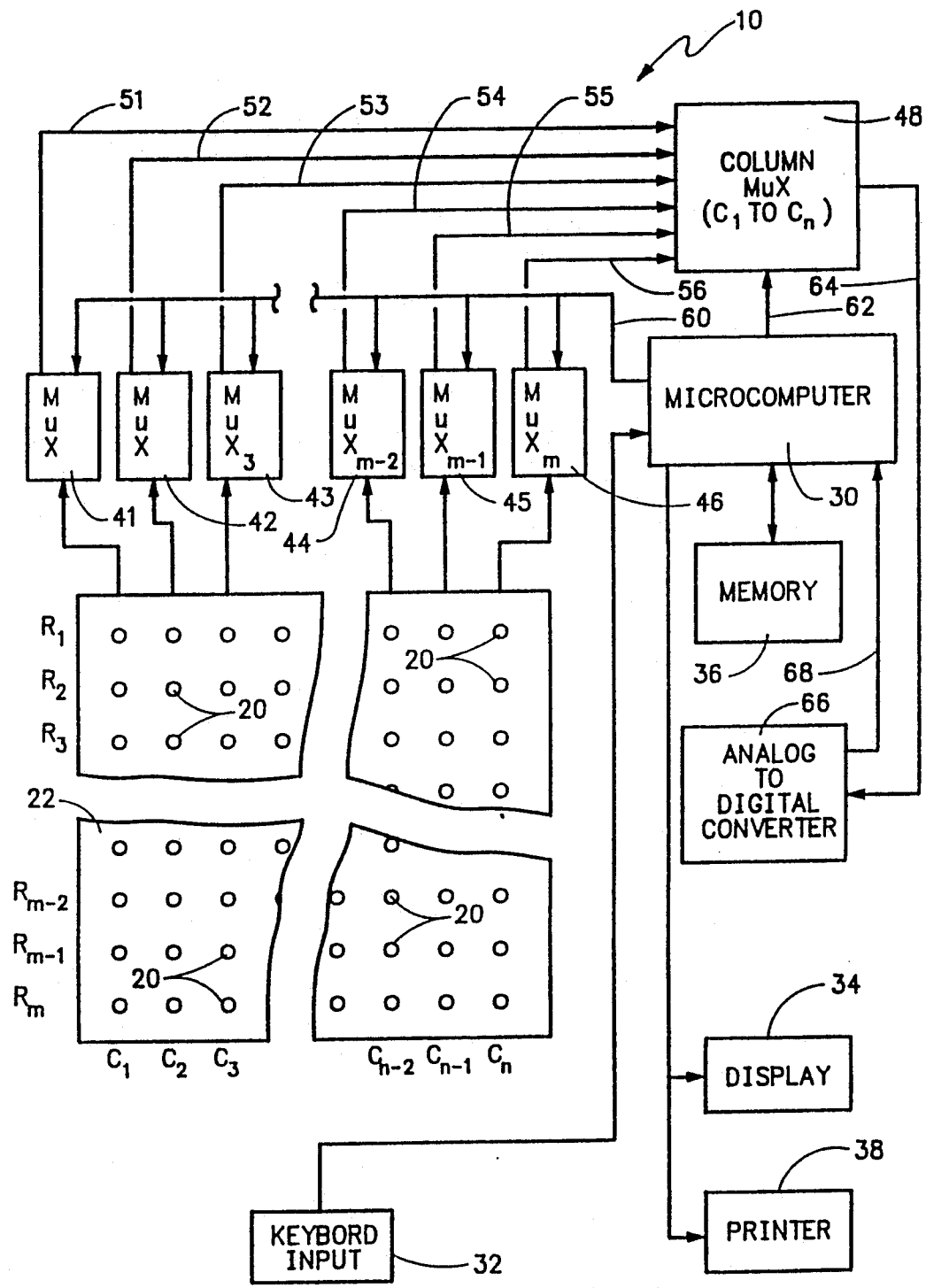
FIG. 1 is a diagrammatic view showing the structure of the pressure monitor apparatus according to the broad form of the invention.

In its broad form as is shown in FIG. 1, pressure monitoring apparatus 10 includes a plurality of pressure sensors 20 which are organized in an array which, as is shown in FIG. 1, can be an $m \times n$ matrix having m rows and n columns designated, respectively, $R_1$-$R_m$ and $C_1$-$C_n$. Pressure sensors 20 can be maintained in the array by being supported, for example, on a thin sheet 22 of flexible material and generate a force signal proportional to the pressure detected by the sensor. A microcomputer 30 is used to monitor the array of pressure sensors 20 and, to this end, has associated therewith a keyboard input 32 a display 34 and a memory means 36. Further, as desired, microcomputer 30 can drive a printer 38 all as is known in the art.

Microcomputer 30 accesses the array of pressure sensors 20 by means of multiplexing circuitry which includes a column multiplexer 48 and row multiplexers 41-46. It should be appreciated that, while FIG. 1 shows six multiplexers 41-46, it should be appreciated that, in this exemplary embodiment, there is a row multiplexer provided for each column in the array. Each row multiplexer is operative to access each of the sensors in its column by row position. Thus, for example, row multiplexer 41 accesses the sensors in column $C_1$ so that the output of multiplexer 41 on line 51 corresponds to the row position of selected pressure sensor in column $C_1$. The selection of the row position for each of the columns is controlled by microcomputer 30 over command line 60. Thus, microcomputer 30 requests an access to the selected row so that each of multiplexers 41-46 provides the pressure signal from the pressure sensor having that row position in the specific column accessed by the respective row multiplexers 41-46. This data is provided, then, on output lines 51-56 which respectively correspond to each of row multiplexers 41-46. Thus, data lines 51-56 each carry a force signal corresponding to a set of pressure sensors in a given row.

A column multiplexer 48 is provided to multiplex data lines 51-56 so as to select a specific data line 51-56 as commanded by microcomputer 30 over command line 62. Thus, a force signal may be presented on data line 64. Pressure data on data line 64 accordingly corresponds to a specific pressure sensor in the array as controlled by the row selected by multiplexers 41-46 and the column selected by multiplexer 48. Since pressure sensors 20 are typically analog devices, the pressure data signal or force signal on data line 64 is an analog signal which is proportional to the pressure sensed by each of sensors 20. This signal is supplied to an analog to digital converter 66 which then supplies a digital force signal to microcomputer 30 by way of data line 68.

From the foregoing, it may now be seen that microcomputer 30 may receive from the array of pressure sensors 20 force signals corresponding to the force of pressure monitored by each of sensors 20 by executing a "read event" which may be defined as a scan of the array of pressure sensors to derive a force profile correlated to the location of each pressure sensor and the respective force detected thereby. Here, for example, microcomputer 30 may command each of row multiplexers 41-46 to provide pressure data from the first row after which microcomputer 30 then commands multiplexer 48 to supply the analog signal from each of lines 51-56, consecutively. The microcomputer may store this pressure information, digitilized by analog to digital computer 66, in memory 38 with this data being correlated to each sensor in row $R_1$. Microcomputer 30 may then command multiplexers 41-46 to supply data from row $R_2$ and again read this data by commanding multiplexer 48 to read data on data lines 51-56. This process repeats for each row $R_1$-$R_m$. At the completion of the read event, memory 36 has stored pressure data corresponding to each of the sensors as it existed at the time of the read event. This array of data thus comprises a force profile for the pressure distribution across the array of sensors 20 on sheet 22. This data can be displayed in a variety of formats; the data may also be interpolated to give pressure estimates between sensor locations.

As shown in FIG. 2 this pressure monitoring apparatus has advantages in monitoring the pressure between a body part and a contact surface. In FIG. 2, it may be seen that a patient 70 is reclining on a bed 72, and pressure sensor sheet 22 is disposed between the torso of patient 70 and the upper surface of bed 72. Sheet 22 is connected to microcomputer 30 by means of interface circuitry 74 that includes the row multiplexers 41-46 (or such other number of row multiplexers as needed) as well as column multiplexer 48. Further, interface circuitry 74 contains a power supply which produces a voltage signal which is modulated by each of pressure sensors 20 proportionately to the force sensed thereby. Interface circuitry 74 is connected to the array of pressure sensors by means of a cable harness 76 which is electrically connected to the array of sensors by means of electrical connector 78. The command lines as well as data line 64 are included within cable harness 80. Keyboard input 32 may be used to command microcomputer 30 to execute a read event or otherwise to program microcomputer 30 to automatically execute one or more read events at a selected time or times. It should be fully understood that the manner of executing a read event and the order in which data is received from each of pressure sensors 20 may be fully controlled by the programming of microcomputer 30. The force profile of a read event may be displayed on display screen 34 or may be output in hard form by means of printer 38, all as is known in the art.

FIG. 3 shows another example of use of pressure sensors 20 on sheet 22 wherein here sheet 22 is wrapped around the lower portion of an arm 90 of a patient wearing a cast 92. In FIG. 3 it may be appreciated that pressure sensors on sheet 22 monitor the pressure between the exterior surface of the forearm and cast 92 which may change over time due to an increase or decrease in swelling or atrophy of the arm. This pressure can be monitored in order to determine any excess pressures which may cause discomfort or injury to the patient.

With reference to FIGS. 2 and 3, it may be seen that pressure sensors 20 can be used to monitor the distribution of weight of a bed ridden patient on a bed to identify any areas of excess pressure that might result in ulceration of the skin.

As noted above, this technique could also be used for other articles of furniture such as wheel chairs and the like. These excess pressures can be used to generate a signal, for example, to notify nursing personnel of a need to redistribute the weight of the bed ridden person or otherwise adjust the contour of the support surface. The monitoring can be performed periodically, on demand, upon the occurrence of a selected event or at any other time within normal system design.

The present invention finds particular utility, as an aide in fitting prosthetic devices on stump portions of a limb. This pressure monitoring apparatus is shown in FIGS. 5-9 as it is used to fit an artificial leg, shown in FIG. 4. Turning, then, to FIG. 4, it may be seen that a prior art artificial leg 100 includes a lower foot portion 101 having a heel portion 102, a ball portion 103 and a toe portion 104 at a distal end thereof. A socket portion 106 is located oppositely foot portion 101 and includes a socket 107 adapted to receive the distal end of leg stump 108 of the human body. A cushioning pad 109 is located between the bottom wall of the socket and the distal end portion of stump 108.

Monitoring the fit between the stump and the artificial leg 100 is best shown in FIGS. 5 and 6. Here, it may be seen that the pressure monitoring apparatus includes interface circuitry 74 which may be contained in a housing 75 that is strap mounted onto a portion of stump 108 by means of fastening strap 112. Wiring 121-126 interconnects interface circuitry 74 with respective pressure strips 131-136, as best shown in FIG. 6. Further, with reference again to FIG. 5, it may be seen that three foot switches are provided on foot portion 101 and include heel switch 114, ball switch 115 and toe switch 116 which are respectively connected to interface circuitry 74 by means of wires 118, 119 and 120.

Figure 7:
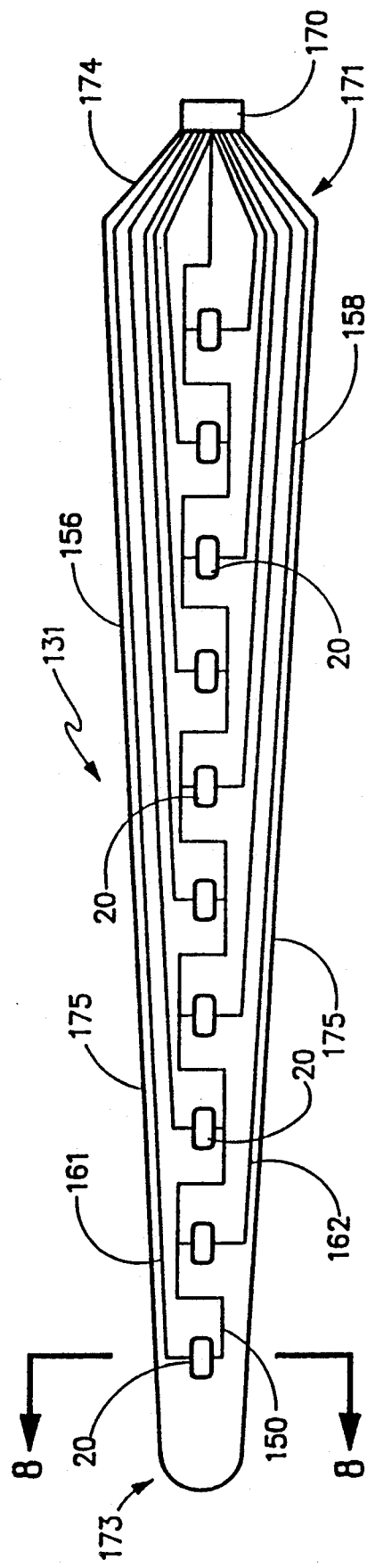
FIG. 7 is a top plan view of a pressure sensor strip according to one exemplary embodiment of the present invention.
Figure 8:
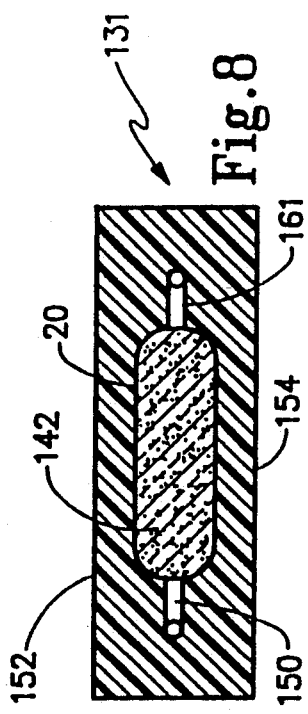
FIG. 8 is a cross-sectional view taken about lines 8—8 of FIG. 7.

Each of strips 131-136 has a similar construction, and a representative strip 131 is shown in FIGS. 7 and 8. Here, it may be seen that strip 131 is tapered from a connector end of 171 to a distal end or tip 173 so that it has side edges 175 that narrow in a direction toward tip 173. When received in socket 107, each of strips 131-136 include a plurality of pressure sensors 20 and are each adapted to extend from bottom wall 138 alongside interior circumferential sidewall 139 thereof. Strips 131-136 may be spaced any desired amount around the sidewall of socket 107 but, as shown in FIG. 6, such spacing may be equidistant from one another. Since the distal portion of the stump of a limb is normally frusto-conical, this tapering of strips 131-136 accommodates the diminishing diameter of socket 107 as it narrows towards bottom wall 140.

Again with reference to in FIGS. 7 and 8, it may be seen that strip 131 is made of a thin durable material such as plastic which provides a support for each of sensors 20. Each sensor 20 is constructed by a pocket 140 of semi-conductive material which changes resistance with pressure. Electrical contact to sensors 20 is made by means of a ground common wire 150 and a respective power wire, such as power lead 161 and 162 are provided to each sensor 20. Each of these power leads and ground wire 150 are bundled together and placed in electrical communication with a connector 170 at connector end 171 to which a respective lead 121-126 may be connected in electrical communication. Pressure on each pocket 142 of semi-conductive material alters its resistance which in turn modulates the voltage signal proportionally to the amount of pressure between upper surface 152 and lower surface 154 of strip 131 at a region proximate pocket 142. Further, as is shown in FIG. 7, sensors 20 are each located midway between left edge 156 and right edge 158 and, to accomplish this positioning, ground wire 150 alternately passes on the left and right of adjacent ones of pressure sensors 20. Other sensor constructions are believed to be known in the art so that other strips or arrays could be substituted for strips 131-136 without departing from this invention.

Figure 9:
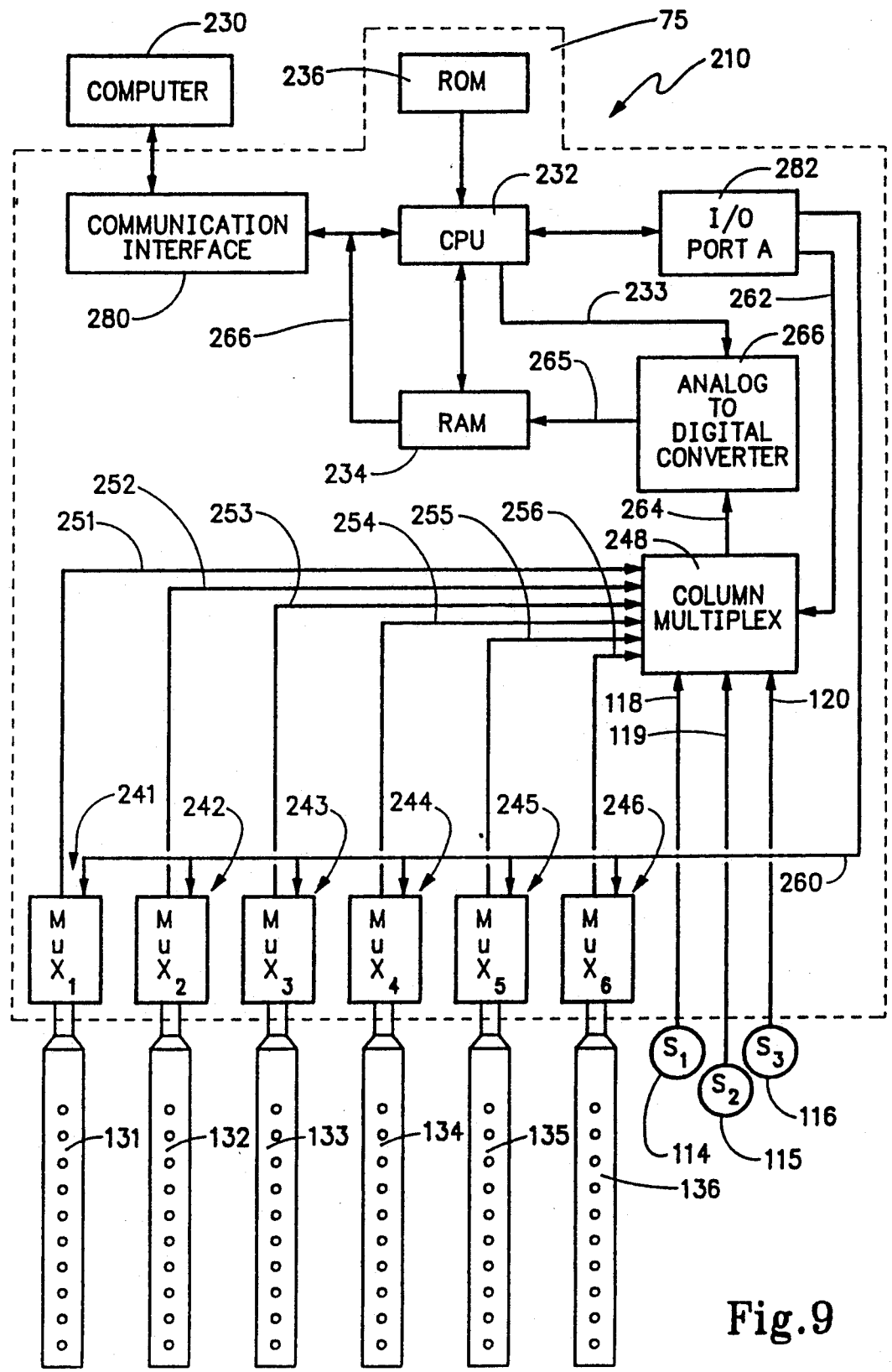
FIG. 9 is a diagrammatic view of the preferred embodiment of the present invention as used in fitting artificial legs.

A more detailed construction of the pressure monitoring apparatus according to the embodiment of this invention as applied to fitting prostheses is shown in FIG. 9. Here, it may be seen that pressure monitoring apparatus 210 is adapted to operate with a plurality of pressure sensing strips 131-136 which, when placed around the sidewall 139 of socket 107, are organized in a cylindrical array similar to the array shown in FIG. 1 with respect to sheet 22. Pressure monitoring apparatus 210 includes processing means in the form of a programmable computer 230 which communicates with a dedicated central processing unit 232 contained within interface circuitry 74. Central processing unit 232 has associated therewith RAM memory 234 and ROM memory 236 and communicates with computer 230 through communications interface 280. Central processing unit 232 has an input/output port 282 which communicates by way of command lead 262 to a column multiplexer 248. Further central processing unit 232 communicates to a plurality of row multiplexers 241-246 by way of a command line 260. Heel switch 114, ball switch 115 and toe switch 116 communicate with central processing unit 232 by way of column multiplexer 248. As was described with respect to FIG. 1, analog signals corresponding to the pressure of the sensors selected by multiplexers 241-246 are presented to multiplexer 248 by way of pressure data lines 251-256. Likewise, the voltage signals from switches 114, 115 and 116 are presented to column multiplexer 248 as analog voltage signals. Column multiplexer 248 presents the selected analog signal according to the access command on command line 262 to analog-to-digital converter 266 over lead 264. Pressure data, in digital form, is then inputted into RAM 234 over data signal line 265 and is then passed over data line 266 to communication interface 280 for presentation to computer 230.

When executing a read event, the operation of pressure monitoring apparatus 210 is the same as that described with pressure monitoring apparatus 10, but it may now be seen that interface circuitry 74 is provided in FIG. 9. Upon transmission a read signal from computer 230 to central processing unit 232 that computer 230 is ready to receive pressure data correlated to the location of the pressure sensors as a read event, central processing unit 232 executes a read event according to its program as stored in ROM 236. When used in conjunction with the various switches 114, 115 and 116, processing unit first sets column multiplexer 248 to monitor input line 118 and sets a flag on line 233. When a person walks on leg 100, the next heel strike after the read signal generates a voltage signal from switch 114, and a read event is executed by scanning the array of pressure sensors. Here, a command signal is given over command line 260 to each of multiplexers 241-246 to output the force signal from the first pressure sensor in its respective strip onto data lines 251-256. Processing unit 232 then increments column multiplexer 248 to consecutively read the analog values on lines 251-256 and output the same on data line 264. This data is converted to digital data by analog to digital converter 266 and stored in RAM 234. Processing unit 232 then indexes multiplexers 241-246 to read the next sensor in its respective strip and again cycles multiplexer 248 to read these values into RAM 234. The pressure signal data from a read event is outputted by RAM 234 as an output signal through communication interface 280 so that it may be received and stored, in whatever format desired, by computer 230. Since communication interface 230 normally operates at slower data transfer speeds, it is necessary that the data from the read signal be stored in RAM 234 so that a read event can be accomplished in the minimum amount of time without waiting for the delay of data transfer through communications interface 280. Once the read even corresponding to the activation of switch 114 has occurred, the system may be reset by processing unit 232 so that a second read event is taken when ball switch 115 becomes active, in the manner described above. This again repeats for a toe strike when toe switch 116 is activated.

It should be appreciated from the foregoing that the manner in which pressure monitoring occurs, as it relates to the taking of data from the array of sensors, may be varied and still fall within the scope of this invention. With the method described above, data according to the coordinates of the pressure sensors is read in a row by row manner which would correspond to reading a circular ring of sensors around the leg, when strips 131-136 are disposed as shown in FIG. 6. However, it would be just as easy to read each column of pressure sensors consecutively as opposed to each row. Further, pressure monitoring apparatus 210 could be programmed to execute a read event cyclically at a selected time. Or activated to execute a single read event regardless of the activation of switches 114-116, for example, when a person is standing, sitting or laying down. Monitoring could be accomplished for walking motion of a person wherein a read event is executed each time a heel, ball and/or toe strike occurs, or a single set of read events corresponding to the heel, ball and toe strikes could be executed as desired. Thus, the ordinarily skilled person in this field should recognize that pressure data may be monitored in a variety of techniques.

Once data is stored in computer 230, it may be outputted in a variety of manners. For example, the pressure data according to a read event could be presented on a display such as display 234 or printed out by printer 38, as is shown in FIG. 2. Where outputted on a visual display, a three-dimensional graph of the pressure distribution about the exterior surface of the body parts could be displayed using known computer aided design techniques. In any event, the pressure data may be used to help fit the stump configuration to the socket configuration on an artificial limb by observing the pressure distribution and re-shaping the configuration of cavity of 107, for example, to remove sidewall material at areas of excess pressure along side 108 that are observed during standing, sitting and walking. Also, as discussed with respect to FIGS. 2 and 3, monitoring of excessive pressure may be used to prevent ulceration of the skin or other unwanted pain associated with excess localized pressure at a specific location between an article of furniture, a cast, etc. and a body part.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. Apparatus adapted to monitor pressure at a plurality of locations along an exterior surface of a body part to produce a force profile corresponding to a distribution of force caused by pressure of said body part against a contact surface, comprising:
   (a) a plurality of pressure sensors organized in an array on at least one strip of flexible substrate material conformable to the contour of the exterior surface of said body part such that said sensors are adapted to be interposed between and in contact with both the exterior surface of said body part and said contact surface at selected locations at which pressure is to be monitored, each of said sensors operative in response to compressive pressure between the exterior of said body part and said contact surface at its respective location to generate a force signal proportional to the pressure therebetween;
   (b) monitor means in communication with the array of said sensors for receiving the force signal produced by each respective said sensor and for producing an output signal having pressure data corresponding to the pressure sensed by the respective said sensor, said monitor means including address means for addressing each of said sensors in said array with a unique address corresponding to its position in said array;
   (c) processing means in communication with said monitor means for receiving and processing the output signals to produce the force profile defining the distribution of force corresponding to the magnitude and location of pressure exerted between the contact surface and the exterior surface of said body part, said processing means including command means for generating a read signal operative to cause said monitor means to produce a set of said output signals correlated to each sensor and to communicate said set of output signals to said processing means as a read event; and
   (d) a plurality of switch means each operative to produce a switch active signal when in an active state, said monitor means operative after receipt of said read signal to initiate a read event in response to each switch active signal.

2. Apparatus according to claim 1 wherein said array is organized in a row and column format with the unique address of each sensor being represented by its row and column position.

3. Apparatus according to claim 2 wherein said monitor means consecutively communicates said output signals to said processing means upon receipt of the read signal.

4. Apparatus according to claim 3 wherein said monitor means consecutively communicates to said processing means the output signals correlated to each of said sensors in a row-by-row order.

5. Apparatus according to claim 1 wherein said processing means has memory means for storing the pressure data from each of said sensors during each said read event with said data being correlated to the address of each respective said sensor.

6. Apparatus according to claim 1 wherein said force signals are analog force signals, said monitor means including converter means for converting said analog force signals to digital force signals.

7. Apparatus according to claim 1 wherein said sensors are mounted to a plurality of strips adapted to be spaced apart from one another along the exterior surface of said body part.

8. Apparatus according to claim 7 wherein each of said strips define a column in the array of said sensors.

9. Apparatus according to claim 1 wherein the array of said sensors is adapted to monitor pressure between a prosthesis and a stump, said contact surface being a portion of said prosthesis interfacing said prosthesis to said stump.

10. Apparatus according to claim 1 wherein the array of said sensors is adapted to monitor pressure between said body part and a cast receiving said body part, said contact surface being a interior surface of said cast.

11. Apparatus according to claim 1 wherein the array of said sensors is adapted to monitor pressure between an article of furniture and a body, the contact surface defined by a support surface of said article of furniture and said body part being defined by a portion of the body contacting the support surface.

12. Apparatus according to claim 11 where said sensors are supported in a two dimensional array on a sheet of flexible substrate material that is adapted to be disposed between the support surface and said body part so that said sheet conforms to the contour of the exterior surface of said body part to position each of said sensors at its selected location therealong.

13. A method of fitting a prosthesis on a stump of a person wherein said prosthesis has a socket formed by a bottom wall and a surrounding sidewall adapted to receive a distal end portion of said stump so that an exterior surface of said distal end portion contacts said surrounding sidewall, comprising the steps of:
  (a) disposing a plurality of pressure sensors at selected locations along said sidewall, each of said sensors operative in response to pressure to produce a force signal proportional to the magnitude of pressure;
  (b) inserting the distal end of said stump into the socket so that said sensors are each sandwiched between said sidewall and the exterior surface of said distal end portion;
  (c) monitoring the force signals from said sensors which result from pressure produced between said sidewall and the exterior surface of the distal end of said stump as a read event at a selected time during an interval within which the person employs said prosthesis whereby each respective force signal is used to generate an output signal indicative of the pressure sensed by the respective sensor;
  (d) receiving said output signals and storing pressure data in response thereto with said pressure data correlated to the location of each respective sensor and the pressure sensed thereby;
  (e) displaying said pressure data as said force profile corresponding to the magnitude and location of pressure exerted by the sidewall on the exterior surface of the distal end portion of said stump at the selected time; and
  (f) re-shaping the socket of said prosthesis to equalize the force of pressure sensed by each of said sensors thereby to fit said prosthesis on said stump.

14. The method according to claim 13 wherein said sensors are disposed in circumferential rings around the distal end portion of said stump.

15. The method according to claim 13 wherein said prosthesis is an artificial leg having a foot with heel, ball and toe portions, and including the steps of providing at least one switch on said foot which activates upon contact of said foot with a walking surface, and initiating said read event upon activation of said switch as the person walks on said artificial leg.

16. The method according to claim 13 including the step of providing a heel switch, a ball switch and a toe switch respectively on said heel, ball and toe portions, said switches respectively activating as its respective heel, ball and toe portion strikes the walking surface, and including the step of initiating a read event upon activation of each of said switches with said pressure data further correlated to the activation of the respective switch.

* * * * *